(12) United States Patent
Thompson et al.

(10) Patent No.: US 8,481,119 B2
(45) Date of Patent: Jul. 9, 2013

(54) BISAMINEAZAALLYLIC LIGANDS AND THEIR USE IN ATOMIC LAYER DEPOSITION METHODS

(75) Inventors: David Thompson, San Jose, CA (US); Jeffrey W. Anthis, San Jose, CA (US)

(73) Assignee: Applied Materials, Inc., Santa Clara, CA (US)

( * ) Notice: Subject to any disclaimer, the term of this patent is extended or adjusted under 35 U.S.C. 154(b) by 43 days.

(21) Appl. No.: 13/189,644

(22) Filed: Jul. 25, 2011

(65) Prior Publication Data

US 2012/0107502 A1 May 3, 2012

Related U.S. Application Data

(60) Provisional application No. 61/407,970, filed on Oct. 29, 2010.

(51) Int. Cl.
  *C23C 16/18* (2006.01)
  *C07F 11/00* (2006.01)
  *H01L 21/31* (2006.01)
(52) U.S. Cl.
  USPC ........ 427/250; 427/248.1; 556/110; 556/137; 556/42; 556/51; 556/57

(58) Field of Classification Search
  None
  See application file for complete search history.

(56) References Cited

U.S. PATENT DOCUMENTS

| | | | | |
|---|---|---|---|---|
| 5,344,948 | A * | 9/1994 | Verkade | 556/51 |
| 2004/0215030 | A1 | 10/2004 | Norman | |
| 2006/0046521 | A1 * | 3/2006 | Vaartstra et al. | 438/778 |
| 2008/0248648 | A1 | 10/2008 | Thompson et al. | |
| 2009/0321733 | A1 * | 12/2009 | Gatineau et al. | 257/43 |
| 2010/0204473 | A1 | 8/2010 | Wolczanski et al. | |

OTHER PUBLICATIONS

Carmalt, J. Mater. Chem, 2003, v13, p. 84-87.*
Lui, Chem. Vap. Deposition, 2001, V7, No. 1, p. 25.*
PCT International Search Report and Written Opinion in PCT/US2011/045177, dated Mar. 9, 2012, 12 pgs.
Volpe, Emily C. et al., "Aryl-Containing Pyridine-Imine and Azaallyl Chelates of Iron Toward Strong Field Coordination Compounds", *Organometallics*, 29 2010, 364-377.

* cited by examiner

*Primary Examiner* — Joseph Miller, Jr.
(74) *Attorney, Agent, or Firm* — Servilla Whitney LLC

(57) ABSTRACT

Methods for deposition of elemental metal films on surfaces using metal coordination complexes comprising bisamineazaallylic ligands are provided. Also provided are bisamineazaallylic ligands useful in the methods of the invention and metal coordination complexes comprising these ligands.

14 Claims, 1 Drawing Sheet

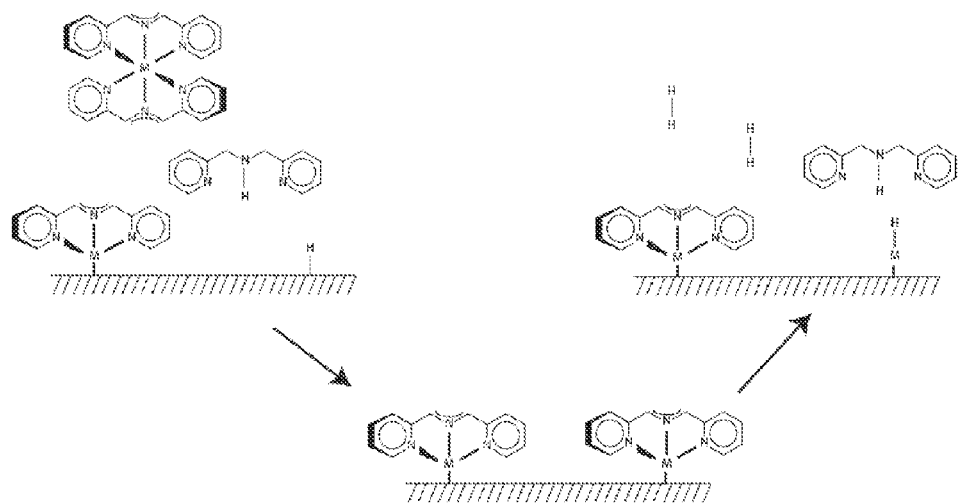

BISAMINEAZAALLYLIC LIGANDS AND THEIR USE IN ATOMIC LAYER DEPOSITION METHODS

TECHNICAL FIELD

The present invention relates generally to methods of depositing thin films of elemental metal and to metal coordination complexes useful in such methods. In particular, the invention relates to coordination complexes of metal cations with multidentate azaallylic ligands and their use in atomic layer deposition processes.

BACKGROUND

Deposition of thin films on a substrate surface is an important process in a variety of industries including semiconductor processing, diffusion barrier coatings and dielectrics for magnetic read/write heads. In the semiconductor industry, in particular, miniaturization requires atomic level control of thin film deposition to produce conformal coatings on high aspect structures. One method for deposition of thin films with atomic layer control and conformal deposition is atomic layer deposition (ALD), which employs sequential, self-limiting surface reactions to form layers of precise thickness controlled at the Ångstrom or monolayer level. Most ALD processes are based on binary reaction sequences which deposit a binary compound film. Each of the two surface reactions occurs sequentially and because they are self-limiting a thin film can be deposited with atomic level control. Because the surface reactions are sequential, the two gas phase reactants are not in contact and possible gas phase reactions that may form and deposit particles are limited. The self-limiting nature of the surface reactions also allows the reaction to be driven to completion during every reaction cycle, resulting in films that are continuous and pinhole-free.

ALD has been used to deposit metals and metal compounds on substrate surfaces. $Al_2O_3$ deposition is an example of a typical ALD process illustrating the sequential and self-limiting reactions characteristic of ALD. $Al_2O_3$ ALD conventionally uses trimethylaluminum (TMA, often referred to as reaction "A" or the "A" precursor) and $H_2O$ (often referred to as the "B" reaction or the "B" precursor). In step A of the binary reaction, hydroxyl surface species react with vapor phase TMA to produce surface-bound $AlOAl(CH_3)_2$ and $CH_4$ in the gas phase. This reaction is self-limited by the number of reactive sites on the surface. In step B of the binary reaction, $AlCH_3$ of the surface-bound compound reacts with vapor phase $H_2O$ to produce AlOH bound to the surface and $CH_4$ in the gas phase. This reaction is self-limited by the finite number of available reactive sites on surface-bound $AlOAl(CH_3)_2$. Subsequent cycles of A and B, purging gas phase reaction products and unreacted vapor phase precursors between reactions and between reaction cycles, produces $Al_2O_3$ growth in an essentially linear fashion to obtain the desired film thickness.

While perfectly saturated monolayers are desired, this goal is very difficult to achieve in practice. The typical approach to further ALD development has been to determine whether or not currently available chemistries are suitable for ALD. Chemistries which have been explored for use in ALD processes include metal halides, metal alkyls, metal alkoxides, beta-diketonates, amides, imido/amido complexes amidinates, cyclopentadienyl complexes and mixed systems of the foregoing compounds. In addition, prior art processes for ALD have been most effective for deposition of metal oxide and metal nitride films. Although a few processes have been developed that are effective for deposition of elemental ruthenium and other late transition metals, in general ALD processes for deposition of pure metal have not been sufficiently successful to be adopted commercially. There is a need for new deposition chemistries that are commercially viable, particularly in the area of elemental metal films. The present invention addresses this problem by providing novel chemistries which are specifically designed and optimized to take advantage of the atomic layer deposition process.

SUMMARY

In one embodiment, the present invention provides methods for producing thin films of elemental metal on a substrate using metal coordination complexes as source material, wherein at least one coordinating ligand is a bisamineazaallylic compound. The thin films may be produced using atomic layer deposition (ALD) processes, including plasma enhanced atomic layer deposition (PEALD) processes. In addition, plasma and thermal ALD processes are both applicable to the methods of the invention.

In an alternative embodiment, the method for producing elemental metal thin films using metal coordination complexes including at least one bisamineazaallylic ligand is a chemical vapor deposition (CVD) process.

In a further embodiment, the metal coordination complexes used in the methods of the invention comprise at least one multidentate bisamineazaallylic ligand. In a specific embodiment the bisamineazaallylic ligand is tridentate. The ligand may be any L as defined below. However, in a further specific embodiment the metal cation of the coordination complex is coordinated with two tridentate bisamineazaallylic ligands, which may be the same (homoleptic) or different (heteroleptic). A specific example of one of the metal complexes formed by coordination with two tridentate bisaminoazaalyllic ligands may be represented by formula (III):

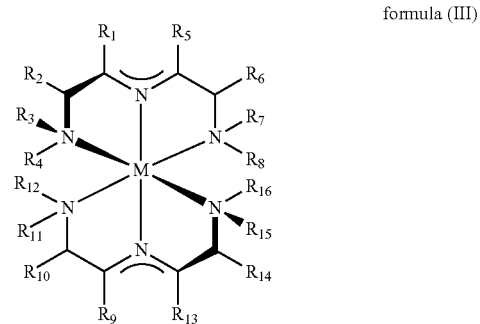

formula (III)

wherein M is a transition metal and each R is independently H, halide, linear or branched $C_{1-6}$ alkyl, acyl, aldehyde, keto, $C_{2-4}$ alkenyl, or is absent thereby forming an adjacent double bond; or one or more of $R_2$ and $R_3$, $R_6$ and $R_7$, $R_{10}$ and $R_{11}$ or $R_{14}$ and $R_{15}$ together with the nitrogen atom to which they are attached form an optionally substituted aromatic or alicyclic ring. The optionally substituted aromatic or alicyclic ring may consist of three, four or five ring carbon atoms.

In a further specific embodiment, at least one tridentate bisamineazaallylic ligand forms two dative M-N bonds (wherein M is the metal cation) and one azaallyl coordination bond with the metal cation. In a further specific embodiment, two tridentate bisamineazaallylic ligands each form two dative M-N bonds (wherein M is the metal cation) and one azaallyl coordination bond with the metal cation. An example of this type of metal coordination complex is represented by formula (IV):

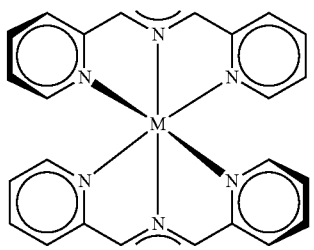

formula (IV)

which is commonly referred to as a bis(bispyridinylazaallylic) metal coordination complex.

In an alternative embodiment, the metal coordination complexes useful in the methods of the invention comprise a single tridentate bisamineazaallylic ligand coordinated with the metal cation and the metal cation is additionally coordinated to at least one neutral or anionic ligand such as halogen (such as Cl), alkyl (such as $C_{1-3}$ alkyl), amido and imido; or to at least one mixed ligand other than an NNN ligand, such as amidinate, amido-amino and pyrollyl-amino.

In another embodiment, the invention provides a method for synthesizing bisamineazaallylic ligands used in the methods of the invention, wherein the synthesis method comprises reacting an aldehyde compound represented by formula $R_1R_2N\text{—}CH_2\text{—}COH$ with a compound represented by formula: $R_3R_4N\text{—}CH_2\text{—}CH_2NH_2$ to form a reaction product represented by formula $R_1R_2N\text{—}CH_2\text{—}CH\text{=}N\text{—}CH_2\text{—}CH_2\text{—}NR_3R_4$. The reaction product is treated with lithium hexamethyldisilazide (LHMDS) to produce the ligand coordinated with a lithium ion. The ligand may then be complexed with the desired transitional metal cation by reaction with the desired transition metal halide.

BRIEF DESCRIPTION OF THE DRAWINGS

The FIGURE illustrates an exemplary ALD process according to the invention.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways. It is also to be understood that the complexes and ligands of the present invention may be illustrated herein using structural formulas which have a particular stereochemistry. These illustrations are intended as examples only and are not to be construed as limiting the disclosed structure to any particular stereochemistry. Rather, the illustrated structures are intended to encompass all such complexes and ligands having the indicated chemical formula.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

L, as used in the formulas disclosed herein, represents a ligand selected from the group consisting of neutral ligands ($L_{neutral}$), anionic ligands ($L_{anionic}$) and mixed ligands ($L_{mixed}$). Examples of neutral ligand molecules include no ligand, carbonyl, amino, bis-(pyridyl) and diamine; examples of anionic ligands include halogen (such as Cl), alkyl (such as $C_{1-3}$ alkyl), amido and imido; and examples of mixed ligands include the NNN ligands of the type disclosed herein, amidinate, amido-amino and pyrolly-amino. As is understood in the art, L may be any combination of $L_{neutral}$, $L_{anionic}$ and $L_{mixed}$ depending on the oxidation state of M. When "L" is used without indication of its charge it is intended to refer generically to all such ligand types.

The term "metal coordination complex" as used herein includes metal chelate complexes wherein a metal ion is coordinated with one or more polydentate ligands and metal coordination complexes wherein a metal ion is coordinated with one or more monodentate ligands. As will be discussed in more detail below, the metal complexes of the invention may consist only of chelating ligands or they may comprise both chelating ligands and coordinating ligands. The term "metal coordination complex" refers to both types of metal complex. The chelate effect of the polydentate ligand provides enhanced affinity for the metal ion in the complex as compared to the affinity of any nonchelating (monodentate) ligands in the complex for the same metal ion.

In general, ligands useful in the elemental metal thin layer deposition methods of the invention include multidentate (chelating) ligands which form at least one bond of covalent character to the metal center and at least one weaker bond to the metal center which involves dative bonding from the ligand. While not intending to be bound by theory, it is believed that the chelate effect helps to stabilize the metal-ligand precursor complex in the vapor phase while maintaining the ability to provide an active site for nucleation of the precursor on a surface.

An ALD process is used in one embodiment of the method of the invention for preparing thin films of elemental metal. In this aspect of the invention the metal coordination complex used in the ALD process is represented by formula (I), which may be referred to herein as an L-(bisamineazaallylic) metal coordination complex:

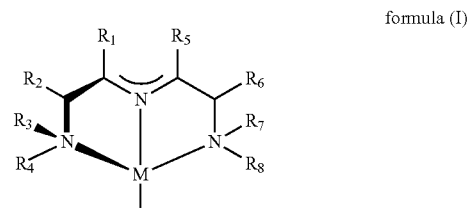

formula (I)

wherein M is a transition metal and each R is independently H, halide, linear or branched $C_{1-6}$ alkyl, acyl, aldehyde, keto, $C_{2-4}$ alkenyl, or is absent thereby forming an adjacent double bond; or one or more of $R_2$ and $R_3$ or $R_6$ and $R_7$ together with the nitrogen atom to which they are attached form an optionally substituted aromatic or alicyclic ring. The optionally substituted aromatic or alicyclic ring may consist of three, four or five ring carbon atoms. L is an M-coordinating ligand as defined above.

An example of a suitable NNN ligand is represented by formula (II):

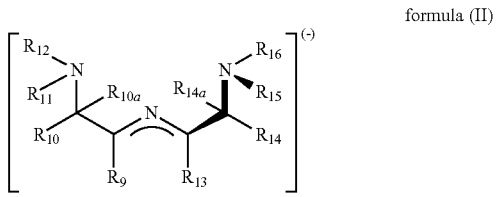

formula (II)

each R is independently H, halide, linear or branched $C_{1-6}$ alkyl, acyl, aldehyde, keto, $C_{2-4}$ alkenyl, or is absent thereby forming an adjacent double bond; or one or more of $R_{10}$ and $R_{11}$ or $R_{14}$ and $R_{15}$ together with the nitrogen atom to which they are attached form an optionally substituted aromatic or alicyclic ring. The optionally substituted aromatic or alicyclic ring may consist of three, four or five ring carbon atoms. It will be recognized that the carbon atom at either $R_{10}/R_{10a}$ or $R_{14}/R14a$, or both, can form a double bond with the adjacent nitrogen in the NNN ligands described herein, and that when either of these carbons forms such a double bond one of $R_{10}$ and $R_{10a}$ or one of $R_{14}$ and R14a will be absent. The ligand represented by formula (II) may be referred to herein as a bisamineazaallylic ligand.

The bisamineazaallylic ligand represented by formula (II) may also be represented in its protonated form by formula (II'):

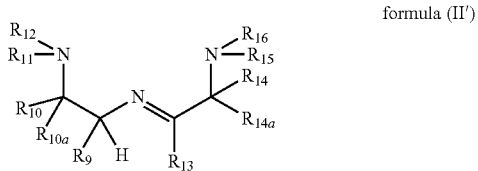

formula (II')

wherein each R is defined as above with respect to formula (II).

The foregoing metal coordination complex wherein L is an NNN ligand may be represented in one aspect by formula (III), which may be referred to herein as a bis(bisamineazaallylic) metal coordination complex:

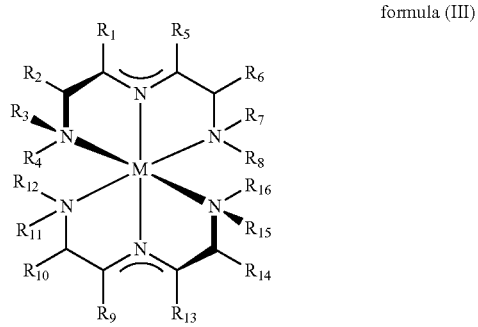

formula (III)

wherein each R is as defined above.

In one embodiment of the metal coordination complex represented by formula (I) for use in the invention, $R_1$, $R_4$, $R_5$ and $R_8$ are independently H, methyl or ethyl, and; $R_2$ and $R_3$, and $R_6$ and $R_7$ together with the nitrogen atoms to which they are attached independently form pyridinyl. If L is an NNN ligand represented by formula (II), in a specific embodiment represented by formula (III) $R_9$, $R_{12}$, $R_{13}$ and $R_{16}$ may also be independently H, methyl or ethyl, and; R10 and $R_{11}$, and $R_{14}$ and $R_{15}$ together with the nitrogen atoms to which they are attached may form pyridinyl.

In a specific embodiment of the metal coordination complex represented by formula (I) for use in the methods of the invention, $R_1$, $R_4$, $R_5$ and $R_8$, are H; and $R_2$ and $R_3$ and $R_6$ and $R_7$ together with the nitrogen atom to which they are attached form pyridinyl. If L is an NNN ligand represented by formula (II), in a specific embodiment represented by formula (III) $R_9$, $R_{12}$, $R_{13}$ and $R_{16}$ may also be independently H, methyl or ethyl, and; R10 and $R_{11}$, and $R_{14}$ and $R_{15}$ together with the nitrogen atoms to which they are attached form pyridinyl.

It is to be understood that, depending on the oxidation state of M, when L is a non-NNN ligand it may represent one or more ligands, each of which may independently be neutral ($L_{neutral}$) or anionic ($L_{anionic}$). For example, L may be three $L_{neutral}$ ligands in a metal (I) coordination complex of the invention, L may be one $L_{anionic}$ and two $L_{neutral}$ ligands in a metal (II) coordination complex of the invention, L may be two $L_{anionic}$ and one $L_{neutral}$ ligand in a metal (III) coordination complex of the invention and L may be three $L_{anionic}$ ligands in a metal (IV) complex of the invention.

In an embodiment of the ALD deposition methods of the invention, a metal coordination complex represented by formula (I) is vaporized and flowed in the vapor phase to a substrate within a deposition chamber. The substrate has a surface that is either activated for reaction with the metal coordination complex or appropriate for adsorption of the metal coordination complex to the surface to form a first layer on the substrate. The reaction between the L-(bisamineazaallylic) metal coordination complex and the surface may occur by an exchange reaction between the surface and the complex to generate H-L and a surface bound metal species. The reaction time, temperature and pressure are selected to create the metal-surface interaction and achieve a layer on the surface of the substrate. The first layer comprises the metal bound to the surface and coordinated with one azaallylic ligand, i.e., in a bisamineazaallylic metal coordination complex. Following formation of the first monolayer, unreacted precursor gas containing the L-(bisamineazaallylic) metal coordination complex and H-L are purged from the deposition chamber using an inert gas. A reducing gas is then flowed into the deposition chamber to reduce the covalent bond between the metal and the azaallylic nitrogen, releasing the second (NNN) ligand and leaving an atomic layer of elemental metal on the substrate. H-(bisamineazaallylic) ligand which is generated is then purged from the chamber.

Optionally, a second atomic layer of elemental metal may be formed on the first atomic layer by repeating the steps of the reaction cycle. Hydrogen remaining from the preceding reduction reaction is purged from the deposition chamber using an inert gas and the metal coordination complex represented by formula (I) in vapor phase is again flowed into the chamber into contact with the metal film on the substrate surface. An exchange reaction may occur between the L-(bisamineazaallylic) metal coordination complex in the vapor phase and the metal of the first atomic layer. This generates H-L and leaves the metal atom of the bisamineazaallylic metal complex bound to the metal atom of the first atomic layer. The reaction time, temperature and pressure are selected to create the metal-metal interaction and produce a layer on the surface of the substrate. Unreacted vapor phase L-(bisamineazaallylic) metal complex and H-L are purged from the deposition chamber using an insert gas. A reducing gas is flowed into the deposition chamber to reduce the covalent bond between the metal and the azaallylic nitrogen, releasing the second ligand and producing a second atomic layer of elemental metal on the first atomic layer of elemental metal. H-(bisamineazaallylic) ligand is then purged from the chamber.

Additional repetitions of the deposition cycle may be used to build a layer of elemental metal of the desired thickness.

A specific embodiment of the method of the invention for preparing thin films of elemental metal is the ALD method illustrated in FIG. 1 which uses as an example a metal coordination complex represented by formula (IV):

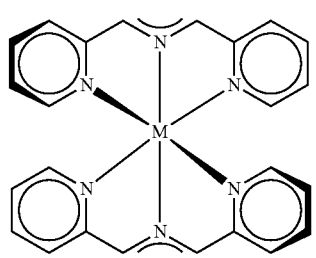

formula (IV)

The coordination complex represented by formula (IV) comprises two di-heteroaryl (pyridinyl) azaallyl ligands as disclosed by Wolczanski, et al. (US PGPub No. 2010/0204473). The surface of the substrate on which the metal film is to be deposited may be an activated surface, illustrated in FIG. 1 as having available hydrogen atoms. The bis(bispyridinylazaallylic) metal complex in vapor phase, optionally in a mixture with an inert carrier gas, is flowed into a deposition chamber containing the substrate and over the substrate surface to effect an exchange reaction wherein a hydrogen atom on the surface displaces one of the two ligands from the metal center. This creates a metal-surface interaction and releases one of the two ligands in the metal coordination complex in reduced form. The surface may be exposed to the bis(bispyridinylazaallylic) metal coordination complex for sufficient time to optimize adsorption on the surface, producing a layer of bispyridinylazaallylic metal coordination complex on the surface.

Unreacted bis(bispyridinylazaallylic) metal coordination complex and released bispyridinylazaallylic ligand in the vapor phase are then typically purged from the ALD system using an inert gas such as nitrogen or argon. Purging is followed by addition of a reducing agent in gaseous form, for example hydrogen gas, which is flowed over the surface so that a second exchange reaction occurs between the hydrogen atoms of the gas and the bispyridinylazaallylic metal coordination complex on the surface. This reaction displaces the second ligand from the surface-bound complex and reduces the atom of metal bound to the surface to elemental form. The second exchange reaction is allowed to proceed for a time sufficient to exchange bispyridinylazaallylic metal coordination complexes on the surface, resulting in an atomic layer of elemental metal.

The ALD system is purged of released ligand and unreacted hydrogen. If a single atomic layer of elemental metal is desired, the process is complete.

Optionally, additional cycles of reacting the bis(bispyridinylazaallylic) metal coordination complex with the surface, purging and reacting the bound bispyridinylazaallylic metal coordination complexes with hydrogen can be performed, each producing an additional atomic layer of elemental metal on the surface. In this way a thin film of the desired thickness can be achieved.

In an alternative embodiment of ALD according to the invention, an $L_{anionic}$-bisamineazaallylic metal coordination complex or a $L_{neutral}$-bisamineazaallylic metal coordination complex is used as the metal source material. In this case the bond between the metal and $L_{anionic}$ or $L_{neutral}$ is reduced by hydrogen atoms on the substrate surface, releasing $HL_{anionic}$ or $HL_{neutral}$ which is purged prior to introduction of the reducing gas. The reducing gas, such as hydrogen, reduces the covalent bond between the metal and the azaallyl nitrogen to release the bisamineazaallylic (NNN) ligand and form the first atomic layer of elemental metal on the surface. Repeating deposition cycles as described above builds the elemental metal thin film to the desired thickness.

In embodiments where the metal coordination complex has sufficient flexibility, disassociation of one of the dative nitrogen-metal bonds may allow an alternative mechanism for deposition of elemental metal thin films. These complexes typically include a bisamineazaallylic ligand represented by formula (V) below in which each R is independently, H, halide, linear or branched $C_{1-6}$ alkyl, acyl, aldehyde, keto, $C_{2-4}$ alkenyl or is absent thereby forming an adjacent double bond; or only one of $R_2$ and $R_3$ or $R_6$ and $R_7$ together with the nitrogen atom to which they are attached form an optionally substituted aromatic or alicyclic ring. In this embodiment, the pendant amine groups can stabilize the metal center but may also readily disassociate to provide an active site for bonding of M with the substrate surface. Such bonding may occur either by adsorption to a bare metal substrate surface or by reaction with an electron donating group. (such as $NH_2$ or OH) on the substrate surface. Remaining coordination bonds (to L and to the bisamineazaallylic ligand) may then be reduced to release the ligands and leave elemental M bound to the substrate surface, generally as described above. Also as described above, deposition cycles may be repeated as necessary to produce an elemental metal film of the desired thickness.

The substrate for deposition of the elemental thin layer films may be any substrate suitable for conformal film coating in an ALD or CVD process. Such substrates include silicon, silica or coated silicon, metals, metal oxides and metal nitrides. In one aspect of the invention, the substrate is a semiconductor substrate.

The L-bisamineazaallylic metal coordination complexes useful in the methods of the invention include as the coordinated metal M any of the transition metals (Groups 3-12 of the periodic table of the elements) or any of the boron group metals (Group 13). Of these, copper, silver, gold, palladium, platinum, rhodium, iridium, tungsten, titanium, zirconium, hafnium, vanadium, niobium, tantalum, chromium, molybdenum, manganese and ruthenium are of particular interest as elemental metal thin films and may be incorporated into the L-bisamineazaallylic metal coordination complexes of the invention as is known in the art based on their oxidation states.

The reaction conditions for the ALD reaction will be selected based on the properties of the selected L-(bisamineazaallylic) metal coordination complex. The deposition can be carried out at atmospheric pressure but is more commonly carried out at a reduced pressure. The vapor pressure of the L-(bisamineazaallylic) metal coordination complex should be high enough to be practical in such applications. The substrate temperature should be low enough to keep the bonds between the metal atoms at the surface intact and to prevent thermal decomposition of gaseous reactants. However, the substrate temperature should also be high enough to keep the source materials (i.e., the reactants) in the gaseous phase and to provide sufficient activation energy for the surface reaction. The appropriate temperature depends on the specific L-(bisamineazaallylic) metal coordination complex used and the pressure. The properties of a specific L-(bisamineazaallylic) metal coordination complex for use in the ALD deposition methods of the invention can be evaluated using methods known in the art, allowing selection of appropriate temperature and pressure for the reaction. In general, lower molecular weight and the presence of functional groups that increase the rotational entropy of the ligand sphere result in a melting point that yields liquids at typical delivery temperatures and increased vapor pressure.

An optimized L-(bisamineazaallylic) metal coordination complex for use in the deposition methods of the invention will have all of the requirements for sufficient vapor pressure, sufficient thermal stability at the selected substrate temperature and sufficient reactivity to produce a self-limiting reaction on the surface of the substrate without unwanted impurities in the thin film or condensation. Sufficient vapor pressure ensures that molecules of the source compound are present at the substrate surface in sufficient concentration to enable a complete self-saturating reaction. Sufficient thermal stability ensures that the source compound will not be subject to the thermal decomposition which produces impurities in the thin film.

Any multidentate ligand represented by formula (V) (also referred to herein as an NNN ligand) with sufficiently high vapor pressure properties may be used in the thin layer film deposition methods of the invention:

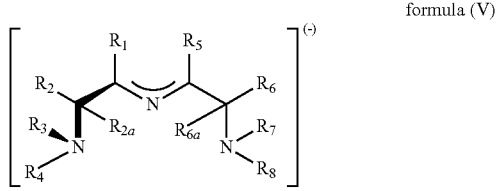

formula (V)

wherein each R is independently, H, halide, linear or branched $C_{1-6}$ alkyl, acyl, aldehyde, keto, $C_{2-4}$ alkenyl or is absent thereby forming an adjacent double bond; or one or more of $R_2$ and $R_3$ or $R_6$ and $R_7$ together with the nitrogen atom to which they are attached form an optionally substituted aromatic or alicyclic ring. The optionally substituted aromatic or alicyclic ring may consist of three, four or five ring carbon atoms. It will be recognized that the carbon atom at either $R_2/R_{2a}$ or $R_6/R_{6a}$, or both, can form a double bond with the adjacent nitrogen in the NNN ligands disclosed herein, and that when either of these carbons forms such a double bond one of $R_2$ and $R_{2a}$ or one of $R_6$ and $R_{6a}$ will be absent.

The bisamineazaallylic ligand represented by formula (V) may also be represented in its protonated form by formula (V'):

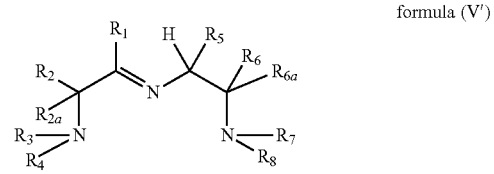

formula (V')

wherein each R is defined as above with respect to formula (V).

In one embodiment of the ligand represented by formula (V), $R_1$, $R_4$, $R_5$ and $R_8$ are independently H, methyl or ethyl; $R_2$ and $R_3$ together with the nitrogen atom to which they are attached form pyridinyl, and; $R_6$ and $R_7$ together with the nitrogen atom to which they are attached form pyridinyl. In a specific embodiment of the ligand represented by formula (V), $R_1$, $R_4$, $R_5$ and $R_8$ are H; $R_2$ and $R_3$ together with the nitrogen atom to which they are attached form pyridinyl, and; $R_6$ and $R_7$ together with the nitrogen atom to which they are attached form pyridinyl.

For use in ALD methods, it is desirable to have a high vapor pressure precursor. With respect to the L-(bisamineazaallylic) metal coordination complexes of the invention, vapor pressure can be optimized by selection of functional groups (R) that minimize the overall molecular weight of the complex: For this reason, in certain specific aspects of the invention the ligands represented by formula (V) each R is independently H, halide, linear or branched $C_{1-6}$ alkyl, acyl, aldehyde, keto, $C_{2-4}$ alkenyl or is absent thereby forming an adjacent double bond. In a further specific aspect, each R is independently H or $C_{1-2}$ alkyl.

Depending on the oxidation state of the selected metal cation, the ligand represented by formula (V) may form a 3-coordinated complex with the metal and one more $L_{neutral}$ or $L_{anionic}$ ligand(s) as defined above may also coordinate M. In a specific embodiment the anionic ligands include Cl, amido or $C_{1-3}$ alkyl and neutral ligands include carbonyl or amino. In an alternative specific embodiment, homoleptic bis(bisaminoazaallyllic) metal complexes may be formed in which two ligands represented by formula (V) coordinate a single metal cation, forming a 6-coordinated complex. However, it is to be understood that L may be an NNN ligand other than one represented by formula (V).

When an $L_{anionic}$-bisamineazaallylic metal coordination complex or an $L_{neutral}$-bisamineazaallylic metal coordination complex is used as the metal source material in the thin film deposition processes of the invention, the bond between the metal and L is reduced by hydrogen atoms on the substrate surface, releasing $HL_{anionic}$ or $L_{neutral}$ which is purged prior to introduction of the reducing gas. The reducing gas, such as hydrogen, reduces the covalent bond between the metal and the azaallyl nitrogen to release the bisamineazallylic (NNN) ligand and form the first atomic layer of elemental metal on the surface.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A method for atomic layer deposition of an elemental metal film comprising contacting a surface of a substrate with a vapor phase metal complex having a formula

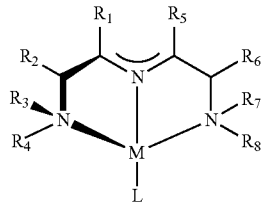

wherein M is a transition metal and each R is independently H, halide, linear or branched C1-6 alkyl, acyl, aldehyde, keto, $C_{2-4}$ alkenyl, or is absent thereby forming an adjacent double bond; or one or more of R2 and R3, and R6 and R7 together with the nitrogen atom to which they are attached form an optionally substituted aromatic or alicyclic ring; and L is a metal coordinating ligand selected from the group consisting of neutral ligands, anionic ligands and mixed ligands;

such that an exchange reaction occurs between the metal complex and the surface, thereby partially dissociating the metal complex and producing a film on the surface comprising the partially dissociated metal complex bound to the surface by M;

contacting the bound metal complex with a reducing gas such that an exchange reaction occurs between the bound metal complex and the reducing gas, thereby dissociating the bound metal complex and producing a layer of elemental M on the surface of the substrate.

2. The method of claim 1, wherein one or more of $R_2$ and $R_3$, and $R_6$ and $R_7$ together with the nitrogen atom to which they are attached form a heteroaryl.

3. The method of claim 2, wherein the heteroaryl is pyridinyl.

4. The method of claim 1, wherein L is an NNN ligand.

5. The method of claim 1, wherein L is a carbonyl, amino, bis-(pyridyl), diamine, halogen, alkyl, amido, imido, amidinate, amido-amino or pyrolly-amino.

6. The method of claim 1, wherein the metal complex is heteroleptic.

7. The method of claim 1, wherein the metal complex is homoleptic.

8. The method of claim 1, wherein the substrate is a semiconductor.

9. The method of claim 1, wherein M is selected from the group consisting of titanium, tungsten, zirconium, vanadium, niobium, tantalum, chromium, molybdenum, palladium, platinum, rhodium, iridium, silver, gold, hafnium, copper, manganese and ruthenium.

10. The method of claim 1, further comprising purging excess unreacted vapor phase metal complex with an inert gas prior to addition of gaseous hydrogen.

11. The method of claim 1, wherein the vapor phase metal complex is in a mixture with an inert gas.

12. The method of claim 1, wherein the metal complex has the formula

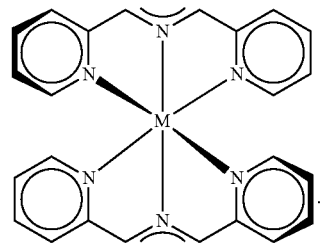

13. The method of claim 1, further comprising contacting the layer of elemental M on the substrate surface with the vapor phase metal complex such that an exchange reaction occurs between the metal complex and the elemental metal, thereby partially dissociating the metal complex and producing a second layer on the surface comprising the partially dissociated metal complex bound to the elemental metal layer by M, and;

contacting the bound metal complex of the second layer with a reducing gas such that an exchange reaction occurs between the bound metal complex and the reducing gas, thereby dissociating the bound metal complex and producing a second layer of elemental M on the surface of the substrate.

14. The method of claim 1, wherein the reducing gas is hydrogen.

* * * * *